(12) United States Patent
Chieh et al.

(10) Patent No.: US 10,527,603 B2
(45) Date of Patent: Jan. 7, 2020

(54) DETECTION METHOD, IMAGING METHOD AND RELATED APPARATUS BASED ON MAGNETISM CHARACTERISTIC DETECTION TECHNIQUE

(71) Applicants: Jen-Jie Chieh, Taipei (TW); Shu-Hsien Liao, New Taipei (TW); Kai-Wen Huang, Taipei (TW); Herng-Er Horng, New Taipei (TW); Hong-Chang Yang, New Taipei (TW); Chin-Yih Hong, Changhua County (TW)

(72) Inventors: Jen-Jie Chieh, Taipei (TW); Shu-Hsien Liao, New Taipei (TW); Kai-Wen Huang, Taipei (TW); Herng-Er Horng, New Taipei (TW); Hong-Chang Yang, New Taipei (TW); Chin-Yih Hong, Changhua County (TW)

(*) Notice: Subject to any disclaimer, the term of this patent is extended or adjusted under 35 U.S.C. 154(b) by 736 days.

(21) Appl. No.: 14/922,204

(22) Filed: Oct. 26, 2015

(65) Prior Publication Data

US 2016/0377575 A1 Dec. 29, 2016

(30) Foreign Application Priority Data

Jun. 29, 2015 (TW) .............................. 104120965 A

(51) Int. Cl.
*G01N 33/483* (2006.01)
*A61B 5/05* (2006.01)
(Continued)

(52) U.S. Cl.
CPC ....... *G01N 33/4833* (2013.01); *A61B 5/0093* (2013.01); *A61B 5/05* (2013.01);
(Continued)

(58) Field of Classification Search
CPC ............ G01N 33/4833; G01R 33/4814; A61B 5/0093; A61B 5/05; A61B 5/01; A61B 8/00
See application file for complete search history.

(56) References Cited

U.S. PATENT DOCUMENTS

| 5,476,438 A | 12/1995 | Edrich et al. |
| 6,817,106 B2 | 11/2004 | Kato |

(Continued)

FOREIGN PATENT DOCUMENTS

| CN | 1814320 | 8/2006 |
| CN | 100429524 | 10/2008 |

(Continued)

OTHER PUBLICATIONS

Fujita et al., "Ultrasonic propagation characteristics of a magnetic fluid under AC magnetic fields", 2014, International Journal of Applied Electromagnetics and Mechanics, pp. 667-673 (Year: 2014).*

(Continued)

*Primary Examiner* — Patrick Assouad
*Assistant Examiner* — Feba Pothen
(74) *Attorney, Agent, or Firm* — JCIPRNET

(57) ABSTRACT

A magnetism characteristic detection method, a magnetism characteristic detection apparatus, an imaging apparatus and an imaging method are provided, where magnetism detection and imaging are based on an integrated excitation field of a direct current (DC) magnetic field and an oscillation wave. The magnetism detection method includes the following steps. A DC magnetic field is selectively applied to an object. Further, an oscillation wave is provided to the object, where the oscillation wave is a sound wave or an ultrasound wave. Then, a magnetism characteristic variation of the object is detected.

14 Claims, 4 Drawing Sheets

(51) Int. Cl.
  *A61B 5/00* (2006.01)
  *A61B 5/01* (2006.01)
  *A61B 8/00* (2006.01)
  *G01R 33/48* (2006.01)
(52) U.S. Cl.
  CPC . *A61B 5/01* (2013.01); *A61B 8/00* (2013.01); *G01R 33/4814* (2013.01)

(56) References Cited

U.S. PATENT DOCUMENTS

| | | | | |
|---|---|---|---|---|
| 2007/0139137 | A1* | 6/2007 | Muniraju | G01D 5/485 333/141 |
| 2009/0043198 | A1* | 2/2009 | Milner | A61B 5/0048 600/437 |
| 2013/0345547 | A1* | 12/2013 | Vahala | G01R 33/4808 600/411 |
| 2015/0301139 | A1* | 10/2015 | Shames | G01N 24/08 324/309 |

FOREIGN PATENT DOCUMENTS

| | | |
|---|---|---|
| EP | 2671091 | 12/2014 |
| JP | 2001074567 | * 3/2001 |
| TW | 418372 | 1/2001 |
| TW | 200638912 | 11/2006 |
| TW | I422356 | 1/2014 |
| TW | I429935 | 3/2014 |
| TW | I432227 | 4/2014 |

OTHER PUBLICATIONS

"Office Action of Taiwan Counterpart Application", dated Sep. 21, 2016, p. 1-p. 5, in which the listed references were cited.
"Office Action of Taiwan Counterpart Application", dated Mar. 14, 2016, p. 1-p. 7, in which the listed references were cited.

* cited by examiner

DETECTION METHOD, IMAGING METHOD AND RELATED APPARATUS BASED ON MAGNETISM CHARACTERISTIC DETECTION TECHNIQUE

CROSS-REFERENCE TO RELATED APPLICATION

This application claims the priority benefits of Taiwan application serial no. 104120965, filed on Jun. 29, 2015. The entirety of the above-mentioned patent application is hereby incorporated by reference herein and made a part of this specification.

BACKGROUND OF THE INVENTION

Field of the Invention

The invention relates to a detection method, an imaging method and related apparatus, and particularly relates to a magnetism characteristic detection method, a magnetism characteristic detection apparatus, an imaging apparatus and an imaging method.

Description of Related Art

In a traditional direct current (DC) magnetism characteristic detection method, a motor and an oscillation rod are generally used to bring oscillation to a sample in a lower oscillation frequency (for example, a frequency below 100 Hz), such that a DC magnetization is converted into an alternating current (AC) magnetic signal, so as to measure a magnetism characteristic variation of the sample through an induction coil. However, the above oscillation type magnetism characteristic detection technique has disadvantages of excessive motor load, high noise, inadequate oscillation amplitude, and easy skew of the oscillation rod, etc., such that the measured magnetism characteristic variation is liable to be distorted, and it is hard to implement investigation on the change of magnetism characteristic of the sample under temperature variation. In other words, a better oscillation type magnetism characteristic detection apparatus and a better oscillation type magnetism characteristic detection method are still a target of effort for related technicians in the field.

On the other hand, the existing AC magnetism characteristic detection method and magnetic imaging technique based on non-DC magnetic signal generally require a high excitation magnetic field and magnetic sensing AC magnetic signals with high sensitivity. Especially, the applied AC excitation magnetic field generally causes a high power consumption of an electromagnet coil. Therefore, to provide an AC magnetism characteristic detection method and a magnetic imaging technique with low power consumption is also a target of effort for related technicians in the field.

SUMMARY OF THE INVENTION

The invention is directed to a magnetism characteristic detection method, a magnetism characteristic detection apparatus, an imaging apparatus and an imaging method. The magnetism characteristic detection method is to perform magnetism characteristic sensing based an integrated excitation field of a direct current (DC) magnetic field and an oscillation wave, so as to provide a magnetism characteristic detection result. Further, the magnetism characteristic detection method and the magnetism characteristic detection apparatus of the invention are easy to be implemented, and temperature control of a detected object is implemented, and a better sensitivity is achieved. The imaging apparatus and the imaging method provided based on the same magnetism characteristic detection technique have lower power consumption, and are easy to be integrated with other imaging method to achieve a good imaging effect.

An exemplary embodiment of the invention provides a magnetism characteristic detection method, which is adapted to detect a magnetism characteristic of at least one object. The magnetism characteristic detection method includes following steps. A direct current magnetic field is selectively applied to the object to magnetize the object. An oscillation wave is provided to the object, wherein the oscillation wave is a sound wave or an ultrasound wave. Then, a magnetism characteristic variation of the object is detected to provide a magnetism characteristic detection result.

An exemplary embodiment of the invention provides a magnetism characteristic detection apparatus, which is adapted to detect a magnetism characteristic of at least one object. The magnetism characteristic detection apparatus includes a direct current magnetic field generating apparatus, an oscillation wave source and an induction coil. The direct current magnetic field generating apparatus is configured to selectively apply a direct current magnetic field to the object to magnetize the object. The oscillation wave source provides an oscillation wave to the object, wherein the oscillation wave is a sound wave or an ultrasound wave. The induction coil is set at periphery of the object to detect a magnetism characteristic variation of the object.

An exemplary embodiment of the invention provides an imaging method, which is adapted to image at least one object. The imaging method includes following steps. A direct current magnetic field is applied to the object to magnetize the object. An oscillation wave is provided to the object, wherein the oscillation wave is a sound wave or an ultrasound wave. A magnetism characteristic variation of the object is scanned, and a magnetic imaging image related to the object is generated according to the magnetism characteristic variation of the object.

An exemplary embodiment of the invention provides an imaging apparatus, which is adapted to image at least one object. The imaging apparatus includes a direct current magnetic field generating device, an oscillation wave source, an induction coil and an image processing device. The direct current magnetic field generating device is configured to apply a direct current magnetic field to the object to magnetize the object. The oscillation wave source provides an oscillation wave to the object, wherein the oscillation wave is a sound wave or an ultrasound wave. The induction coil is configured to scan a magnetism characteristic variation of the object in a stationary or moving manner. The image processing device is coupled to the induction coil, and generates a magnetic imaging image related to the object according to the magnetism characteristic variation of the object.

According to the above descriptions, in the magnetism characteristic detection method provided by the exemplary embodiment of the invention, the direct current magnetic field is selectively applied to the object and the oscillation wave is provided to the object, and the magnetism characteristic variation of the object is detected. The oscillation wave is a sound wave or an ultrasound wave. The above magnetism characteristic detection method and the related magnetism characteristic detection apparatus are easy to be implemented, and have better sensitivity. On the other hand, the imaging apparatus and imaging method based on the same magnetism characteristic detection method have lower power consumption, and are easy to be integrated with other imaging methods to achieve a good imaging effect.

In order to make the aforementioned features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
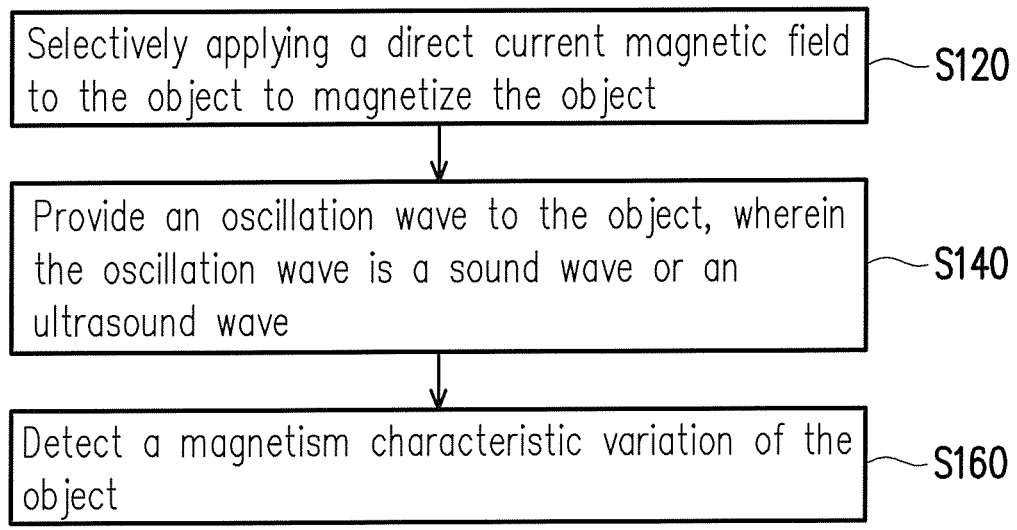
FIG. 1 is a flowchart illustrating a magnetism characteristic detection method according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

In a magnetism characteristic detection method provided by an exemplary embodiment of the invention, an oscillation wave in form of a sound wave or an ultrasound wave is used to oscillate an object, and a magnetism characteristic variation of the object is detected to provide a magnetism characteristic detection result. Compared with the traditional method of using a motor and an oscillation rod to oscillate the object and measure the magnetism characteristic, the magnetism characteristic detection method and a related magnetism characteristic detection apparatus of the invention have higher oscillation frequency, and are easy to produce a higher magnetic induction voltage, which conduce the measurement of the magnetism characteristic variation of the object. Moreover, based on the aforementioned magnetism characteristic detection method, an imaging apparatus and an imaging method provided by other exemplary embodiments of the invention achieve a requirement of low power consumption, and are easy to be integrated with an ultrasound imaging technique to achieve an effect of providing both of functional imaging and structural imaging.

FIG. 1 is a flowchart illustrating a magnetism characteristic detection method according to an embodiment of the invention. Referring to FIG. 1, the magnetism characteristic detection method includes following steps. First, a direct current (DC) magnetic field is selectively applied to an object to magnetize the object (step S120). An oscillation wave is provided to the object, wherein the oscillation wave is a sound wave or an ultrasound wave (S140), and the sound wave and the ultrasound wave are all mechanical waves. Then, a magnetism characteristic variation of the object is detected (S160) to provide a magnetism characteristic detection result.

To be specific, when the magnetism characteristic of an object is detected, it is first determined whether to apply the DC magnetic field to the object to increase magnetization of the object. Then, the oscillation wave implanted by a mechanical wave is provided to the object to oscillate the object. In the present embodiment, the oscillation wave is a sound wave or an ultrasound wave, and a frequency of the oscillation wave is, for example, not lower than 1000 Hz, though the invention is not limited thereto. In other embodiments of the invention, the frequency of the oscillation wave is, for example, selected to be not lower than 20000 Hz, and the oscillation wave is an ultrasound wave. When the object is magnetized and oscillated, the magnetism characteristic thereof is varied along with the oscillation. Now, by sensing the magnetism characteristic variation of the object, the magnetism characteristic detection of the object is completed. On the other hand, imaging can be performed according to the magnetism characteristic variation of the object. The aforementioned magnetism characteristic detection method and related applications thereof are introduced in detail below with reference of a plurality of embodiments.

Figure 2A:
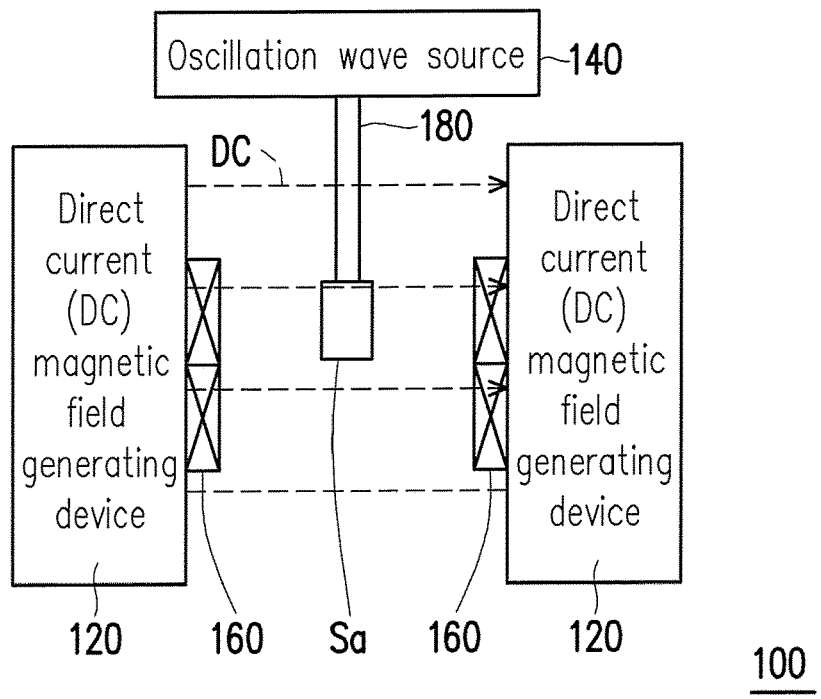
FIG. 2A is a schematic diagram of a magnetism characteristic detection apparatus according to an embodiment of the invention.

FIG. 2A is a schematic diagram of a magnetism characteristic detection apparatus according to an embodiment of the invention. Referring to FIG. 2A, the magnetism characteristic detection apparatus 100 is adapted to detect a magnetism characteristic of an object Sa, and includes a DC magnetic field generating apparatus 120, an oscillation wave source 140, an induction coil 160 and a conduction device 180. The DC magnetic field generating apparatus 120 is disposed at periphery of the object Sa, and is configured to selectively apply a DC magnetic field DC to the object Sa to magnetize the object Sa. The DC magnetic field generating apparatus 120 is, for example, a magnet set without power consumption or an electromagnet set with low power consumption. The oscillation wave source 140 provides an oscillation wave, and conducts the oscillation wave to the object Sa through the conduction device 180. The oscillation wave provided by the oscillation wave source 140 is a sound wave or an ultrasound wave, and a frequency of the oscillation wave is, for example, not lower than 1000 Hz. In another embodiment of the invention, the oscillation wave is preferably an ultrasound wave, and a frequency thereof is not lower than 20000 Hz, and the oscillation wave source 140 is, for example, an ultrasound sheet. It should be noted that in the embodiment of FIG. 2A, although the direction of the DC magnetic field DC and a conducting direction (propagating direction) of the oscillation wave are perpendicular to each other to present a right angle, the invention is not limited thereto. In other embodiments of the invention, the direction of the DC magnetic field DC and the conducting direction (propagating direction) of the oscillation wave can be not perpendicular to each other to present an included angle other than the right angle.

Figure 3:
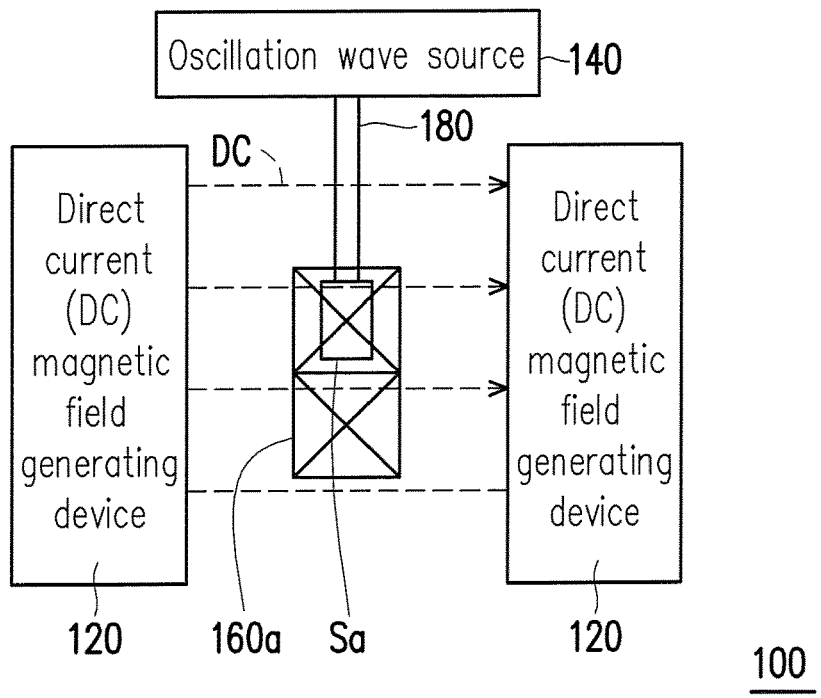
FIG. 3 is a schematic diagram of a magnetism characteristic detection apparatus according to still another embodiment of the invention.

The induction coil 160 is set at periphery of the object Sa to detect a magnetism characteristic variation of the object Sa. In the present embodiment, the induction coil 160 is, for example, a plurality of pairs of planar coils, which are correspondingly set at two sides of the object Sa, and located within the DC magnetic field generating device 120. However, in another embodiment of the invention, if the object is relatively small, the induction coil 160 is, for example, a solenoid coil set. FIG. 3 is a schematic diagram of a magnetism characteristic detection apparatus according to still another embodiment of the invention. As shown in FIG. 3, the induction coil 160a surrounds the object Sa, and is located within the DC magnetic field generating apparatus 120.

To be specific, when the object Sa is disposed in the DC magnetic field DC, the object Sa is magnetized to induce a magnetic moment. When the object Sa is oscillated along with the oscillation wave, due to variation of a magnetic flux, the induction coil 160 or 160a correspondingly senses an induced voltage, and a relationship between the magnetic flux and the induced voltage is as follows.

$$V = -\frac{d\varphi}{dt} = \frac{d[B_0 \sin(\omega t) \cdot A_{coil}]}{dt} = \omega A_{coil} B_0 \cos(\omega t) \quad (1)$$

Where, V (with a unit of volt) is the induced voltage, φ (with a unit of weber) is the magnetic flux, $B_0$ is a magnetic flux density, $A_{coil}$ is a coil induction area and co is a change frequency. According to the equation (1), it is known that a variation of the induced voltage sensed by the induction coils 160 or 160a can be used to calculate the magnetic flux of the object Sa, so as to deduce the magnetism characteristic variation of the object Sa. To be specific, the induced voltage sensed by the induction coil 160 or 160a is further provided to a computer, a server or other computer apparatus connected to the magnetism characteristic detection apparatus 100, and the magnetism characteristic variation of the object Sa is deduced by the computer apparatus.

As described above, in the magnetism characteristic detection apparatus 100, the oscillation wave provided by the oscillation wave source 140 is an ultrasound wave or a sound wave, and has an oscillation frequency not lower than 1000 Hz. Comparatively, regarding the traditional method for driving the object to oscillate through a motor and an oscillation rod, an oscillation frequency thereof is lower than 100 Hz. If variation of other parameters is not considered, according to the equation (1), it is known that when the object Sa is influenced by the oscillation wave to oscillate, the induced voltage sensed by the induction coil 160 or 160a is higher than that sensed by the induction coil when the object is driven by the motor and oscillation rod to oscillate. In other words, the magnetism characteristic detection apparatus 100 of the present embodiment adopts the oscillation wave source 140 to improve sensitivity of magnetism characteristic detection.

Referring to FIG. 2A and FIG. 3, in the magnetism characteristic detection apparatus 100, the oscillation wave is, for example, an ultrasound wave or a sound wave. If the oscillation wave is conducted to the object Sa through a medium such as air, the oscillation wave is easy to attenuate, and is hard to maintain a good oscillation quality. Therefore, in order to suitably conduct the oscillation wave from the oscillation wave source 140 to the object Sa, the conduction device 180 is disposed between the oscillation wave source 140 and the object Sa. One end of the conduction device 180 is in contact with the oscillation wave source 140 and another end of the conduction device 180 is in contact with the object Sa, and the oscillation wave provided by the oscillation wave source 140 is conducted to the object Sa through the conduction device 180.

In the present embodiment, the conduction device 180 is a flexible duct containing a liquid substance, or a flexible rod. The liquid substance includes water, and the flexible duct and the flexible rod are made of a flexible material, where the flexible material includes phantom, silicone, rubber, plastic, nylon and resin. The phantom is, for example, made of pure water, salt water and gelatine. It should be noted that the flexible duct containing the liquid substance or the flexible rod can preferably maintain and conduct the oscillation wave to the object Sa. Moreover, in another embodiment of the invention, the oscillation wave source 140 can be as close to the object Sa as possible, so as to transmit the oscillation wave to the object Sa in case that the conduction device 180 is not presented.

Figure 2B:
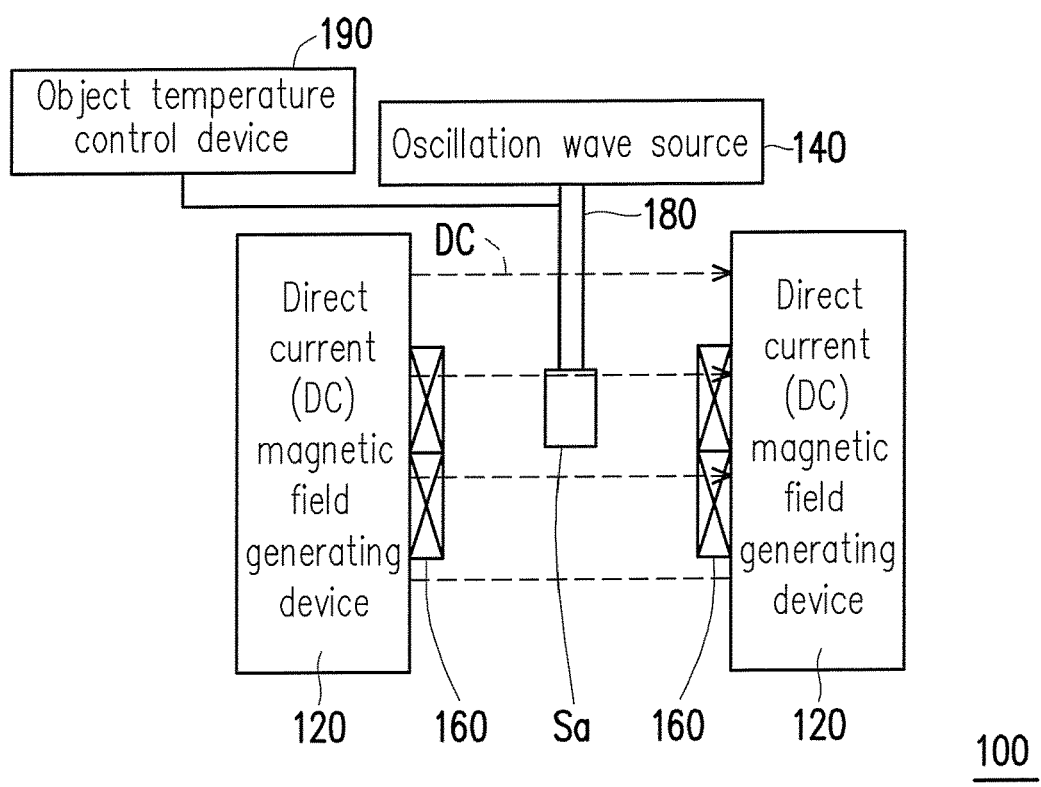
FIG. 2B is a schematic diagram of a magnetism characteristic detection apparatus according to another embodiment of the invention.

In the magnetism characteristic detection, a temperature variation of the object Sa may also influence the magnetism characteristic of the object Sa, so as to influence a detection result. Therefore, to maintain and control the temperature of the object Sa is also an important issue. FIG. 2B is a schematic diagram of a magnetism characteristic detection apparatus according to another embodiment of the invention. Referring to FIG. 2B, in the present embodiment, the magnetism characteristic detection apparatus 100 further includes an object temperature control device 190. The object temperature control device 190 is coupled to the conduction device 180, and controls the temperature of the object Sa while taking the conduction device 180 as a control medium. For example, the object temperature control device 190 is, for example, a heater, which can change the temperature of the object Sa by heating the conduction device 180.

It should be noted that in the aforementioned embodiment, the conduction device 180 is, for example, a flexible duct containing a liquid substance, and the liquid substance is, for example, water. Since a thermal capacity of water is 4200 ($JKg^{-1} K^{-1}$), in an embodiment of the invention, by injecting the water of different temperatures into the flexible duct, the temperature of the object Sa can also be adjusted.

In the aforementioned magnetism characteristic detection apparatus 100 and the magnetism characteristic detection method, the DC magnetic field and the oscillation wave are integrated to detect the magnetism characteristic variation of the object Sa, and the oscillation wave is, for example, a sound wave or an ultrasound wave. In another exemplary embodiment, an imaging apparatus and a related imaging technique are provided based on the magnetism characteristic detection method of FIG. 1.

Figure 4:
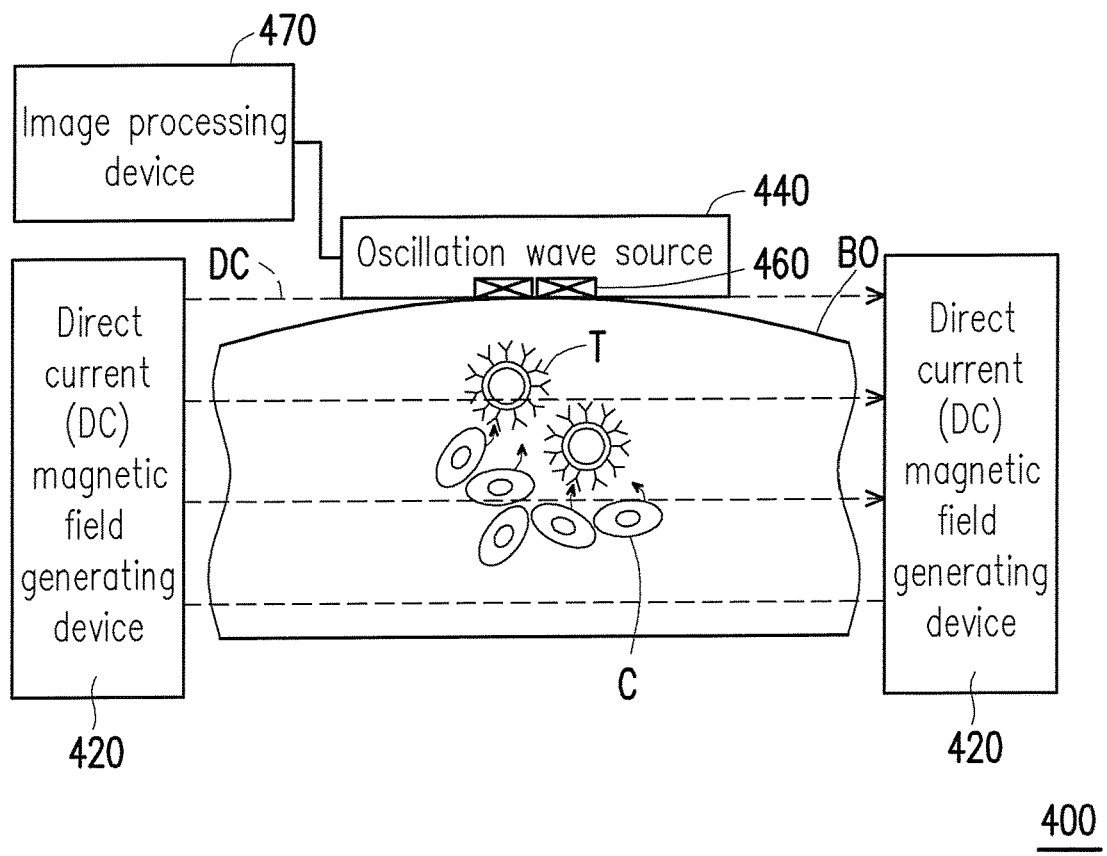
FIG. 4 is a schematic diagram of an imaging apparatus according to an embodiment of the invention.

FIG. 4 is a schematic diagram of an imaging apparatus according to an embodiment of the invention. Referring to FIG. 4, in the present embodiment, the imaging apparatus 400 is adapted to image an object, and the imaging apparatus 400 includes a DC magnetic field generating device 420, an oscillation wave source 440, an induction coil 460 and an image processing device 470. In the present embodiment, the object is, for example, a targeted component T in a biological organism BO, though the invention is not limited thereto. In other embodiments of the invention, the object can be directly the biological organism BO. The DC magnetic field generating device 420 is configured to apply a DC magnetic field to the biological organism BO to magnetize the targeted component T in the biological organism BO or the biological organism BO. In detail, the targeted component T is, for example, magnetic nanoparticles distributed with special bioprobes, which are used for marking cells C having corresponding biomarkers. For example, the targeted component T is used for marking cancer cells having special proteins.

For example, the object is the targeted component T, after the targeted component T is magnetized, the oscillation wave source 440 of the imaging device 400 provides the oscillation wave to the biological organism BO and the targeted component T, where the oscillation wave is, for example, a sound wave or an ultrasound wave. In the present embodiment, a frequency of the oscillation wave is, for example, not lower than 1000 Hz, though the invention is not limited thereto. Now, the targeted component T has a variation in the magnetism characteristic (for example, magnetic flux) in response to the oscillation wave. The oscillation wave source 440 can be attached to or close to a body surface of the biological organism BO to generate the oscillation wave, or the oscillation wave source 440 generates the oscillation wave, and provides the oscillation wave to the biological organism BO through a conduction device (not shown in FIG. 4). In an embodiment of the invention, the oscillation wave source 440 or the conduction device can move along the body surface of the biological organism BO to change the active area of the oscillation wave. It should be noted that in FIG. 4, although the direction of the DC magnetic field DC and the conducting direction (propagating direction) of the oscillation wave are perpendicular to each other to present a right angle, the invention is not limited thereto. In other embodiments of the invention, the direction of the DC magnetic field DC and the conducting direction (propagating direction) of the oscillation wave can be not perpendicular to each other to present an included angle other than the right angle.

The induction coil 460 can be stationary or moves on the biological organism BO to detect a magnetism characteristic variation thereof. It should be noted that when the induction coil 460 scans the targeted component T, an induced voltage on the induction coil 460 should have a larger variation or a larger voltage reading value. The image processing device 470 is coupled to the induction coil 460, and generates a magnetic imaging image related to the targeted component T and the biological organism BO according to the magnetism characteristic variation of the targeted component T and the biological organism BO, respectively. The image processing device 470 is, for example, a computer, a server or other a computer apparatus connected to the induction coil 460 or the imaging apparatus 400. The magnetic imaging is a functional imaging, which can be used to assist seeking the position of specific cells, for example, the position of cancer cells.

It should be noted that based on the selected oscillation wave source 440, the imaging apparatus 400 can easily integrate a magnetic imaging function and an ultrasound imaging function. To be specific, in another embodiment of the invention, the imaging apparatus 400 further includes an oscillation wave detection unit (not shown), and the oscillation wave provided by the oscillation wave source 440 is an ultrasound wave, and a frequency thereof is not lower than 1000000 Hz. The oscillation wave detection unit is coupled to the image processing device 470, and movably contacts with the body surface of the biological organism BO, so as to detect along the body surface of the biological organism BO to obtain a reflected oscillation wave generated by the biological organism BO and the targeted component T by reflecting the oscillation wave. The image processing device 470 generates an oscillation wave imaging image related to the biological organism BO and the targeted component T according to the received reflected oscillation wave. Since the oscillation wave is an ultrasound wave, the oscillation wave imaging image of the present embodiment is the ultrasound wave imaging image, which is a structural imaging. Therefore, the imaging apparatus 400 of the present embodiment can simultaneously provide the magnetic imaging image and the ultrasound imaging image to serve as a reference for post medical diagnosis. On the other hand, the imaging apparatus 400 provided by the above embodiment can be easily integrated with other types of ultrasound wave imaging apparatus to improve the imaging function.

The imaging apparatus 400 provided by the aforementioned embodiment can be used as image guide and further applied to a cautery surgery or a minimally invasive surgery. In a common cautery surgery, radio frequency (RF) energy, microwave energy, a focused ultrasound, or a laser is taken as a burning means, in which a high-intensity focused ultrasound (HIFU) surgery is one of most popular cautery surgeries in recent years. During a process of the cautery implemented through the HIFU, images generated via a magnetic resonance image (MRI) technique are used for guidance. However, the MRI is not only time-consuming but also requires expensive equipment, such that the HIFU surgery cannot avoid a high cost in time and money. However, in the HIFU surgery, if the magnetic imaging images are generated through the imaging apparatus 400 provided by the aforementioned embodiment, the HIFU can be correctly guided to burn a correct tumor position or a diseased part. In this way, the time required for waiting the MRI is saved, and the cost thereof is also reduced.

Figure 5:
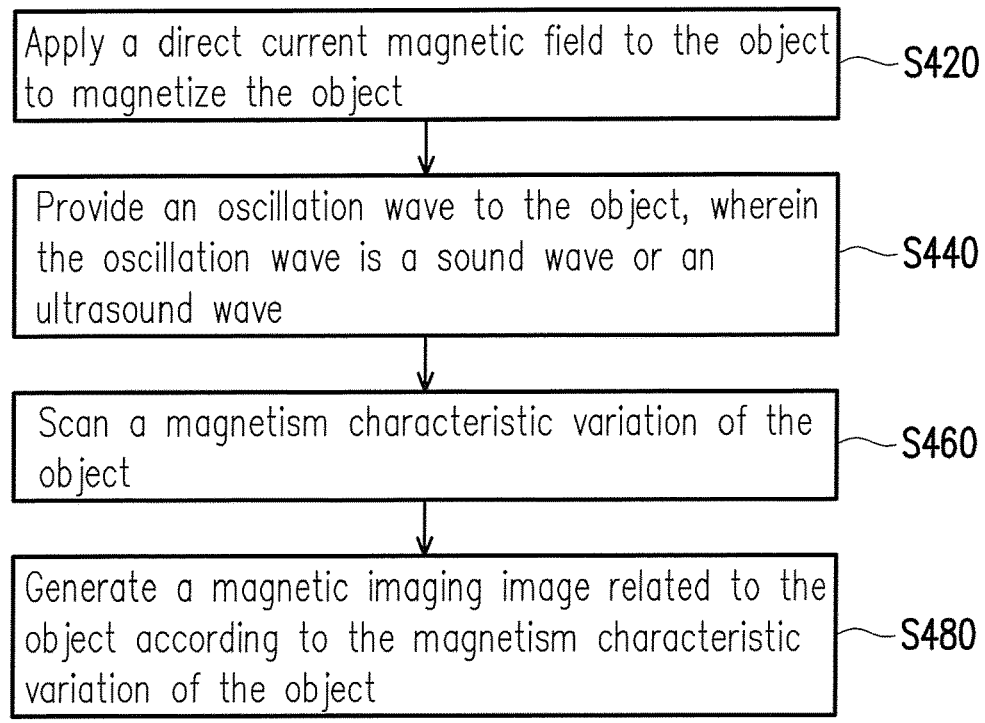
FIG. 5 is a flowchart illustrating an imaging method according to an embodiment of the invention.

FIG. 5 is a flowchart illustrating an imaging method according to an embodiment of the invention. Referring to FIG. 5, the imaging method can be adapted to the imaging apparatus 400 shown in FIG. 4, though the invention is not limited thereto. The imaging method is adapted to image an object, and the object is, for example, the biological organism BO and the targeted component T in the biological organism BO. The imaging method includes following steps. First, the DC magnetic field DC is applied to the object to magnetize the object (step S420). Then, an oscillation wave is provided to the object, wherein the oscillation wave is a sound wave or an ultrasound wave (step S440), and a frequency of the oscillation wave is not lower than 1000 Hz. A magnetism characteristic variation of the object is scanned (step S460), and a magnetic imaging image related to the object is generated according to the magnetism characteristic variation of the object (step S480).

It should be noted that in another embodiment of the invention, the imaging method further includes detecting along a body surface of the object to obtain a reflected oscillation wave generated by the object by reflecting the oscillation wave, and generating an oscillation wave imaging image related to the object according to the received reflected oscillation wave. To be specific, besides that the imaging method provides the magnetic imaging image, the imaging method further provides the ultrasound wave imaging image. Correspondingly, in the present embodiment, the oscillation wave is an ultrasound wave, and the frequency of the oscillation wave is not lower than 1000000 Hz.

Figure 6:
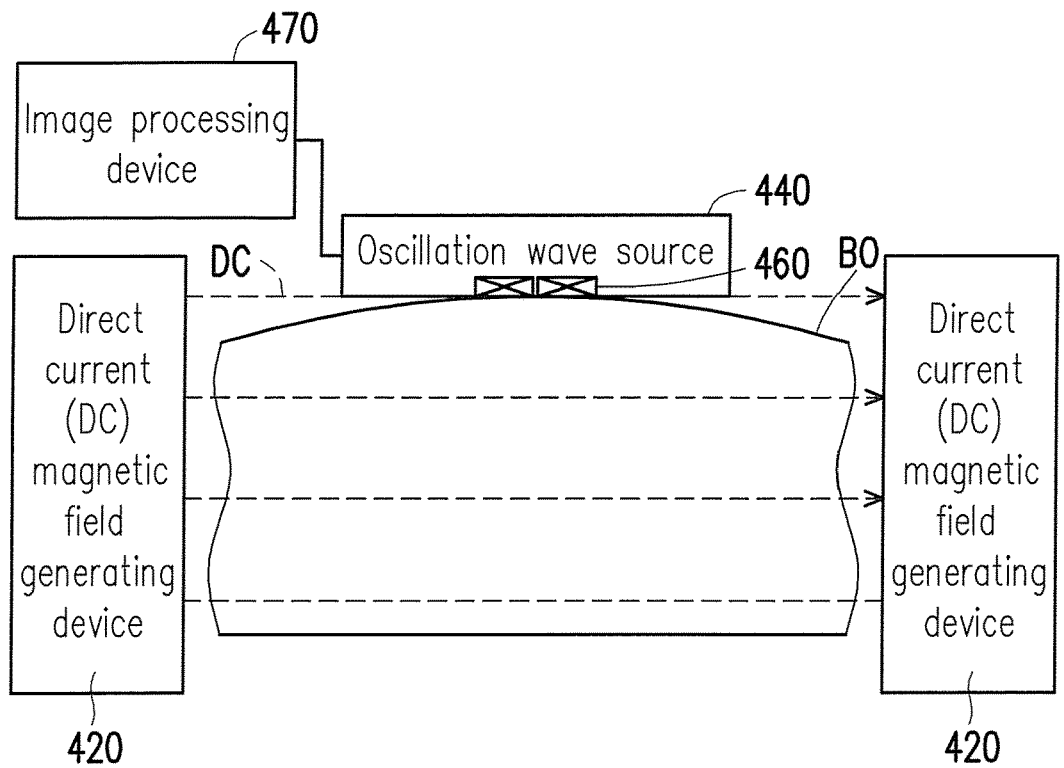
FIG. 6 is a schematic diagram of an imaging method according to another embodiment of the invention.

FIG. 6 is a schematic diagram of an imaging method according to another embodiment of the invention. As described above, in the imaging method, a main magnetization object of the DC magnetic field DC can also be a biological organism BO. To be specific, when the DC magnetic field DC is provided to magnetize the biological organism BO, the oscillation wave source 440 is used to provide an oscillation wave pulse, and the induction coil 460 can receive a magnetic relaxation signal to serve as a nuclear magnetic resonance (NMR) signal. By focusing the oscillation wave to different positions of the biological organism BO, the three-dimensional MRI of the biological organism BO is implemented according to the collected magnetic relaxation signals.

In summary, in the magnetism characteristic detection method provided by the exemplary embodiment of the invention, the DC magnetic field is selectively applied to the object and the oscillation wave is provided to the object, and then the magnetism characteristic variation of the object is detected. The oscillation wave is a mechanical wave such as a sound wave or an ultrasound wave. The above magnetism characteristic detection method and the related magnetism characteristic detection apparatus conduct the oscillation wave to the object through a conduction device, and the conduction device is, for example, a flexible duct containing a liquid substance or a flexible rod. The object temperature control device controls the temperature of the object through the conduction device. In this way, the magnetism characteristic detection device and the magnetism characteristic detection method are easy to be implemented, and have better sensitivity and can effectively control the temperature of the object. On the other hand, the imaging apparatus and the imaging method based on the same magnetism characteristic detection method have lower power consumption, and are easy to be integrated with other imaging methods to achieve a good imaging effect.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A magnetism characteristic detection method, adapted to detect a magnetism characteristic of at least one object, the magnetism characteristic detection method comprising:
   selectively applying a direct current magnetic field to the object to magnetize the object;
   providing an oscillation wave to the object to generate an oscillation on the object, wherein the oscillation wave is a sound wave or an ultrasound wave; and
   detecting a magnetic flux of the object directly using an induction coil surrounding the object in order to obtain a variation of the magnetism characteristic of the object caused by the oscillation.

2. The magnetism characteristic detection method as claimed in claim 1, wherein the step of providing the oscillation wave to the object to generate the oscillation on the object comprises:
   conducting the oscillation wave to the object through a conduction device,
   wherein the oscillation wave is provided by an oscillation wave source, the conduction device is set between the oscillation wave source and the object, one end of the conduction device contacts with the oscillation wave source, another end of the conduction device contacts with the object, and the conduction device is a flexible duct containing a liquid substance or a flexible rod, wherein the liquid substance comprises water, the flexible duct and the flexible rod are made of a flexible material, and the flexible material comprises phantom, rubber, silicone, plastic, nylon and resin.

3. The magnetism characteristic detection method as claimed in claim 2, further comprising:
   controlling temperature of the object by taking the conduction device as a control medium.

4. A magnetism characteristic detection apparatus, adapted to detect a magnetism characteristic of at least one object, the magnetism characteristic detection apparatus comprising:
   a direct current magnetic field generating apparatus, selectively applying a direct current magnetic field to the object to magnetize the object;
   an oscillation wave source, providing an oscillation wave to the object to generate an oscillation on the object, wherein the oscillation wave is a sound wave or an ultrasound wave; and
   an induction coil, set at periphery of the object to detect a magnetic flux of the object directly in order to obtain a variation of the magnetism characteristic of the object caused by the oscillation.

5. The magnetism characteristic detection apparatus as claimed in claim 4, further comprising:
   a conduction device, set between the oscillation wave source and the object to conduct the oscillation wave to the object, wherein one end of the conduction device contacts with the oscillation wave source, another end of the conduction device contacts with the object, and the conduction device is a flexible duct containing a liquid substance or a flexible rod, wherein the liquid substance comprises water, the flexible duct and the flexible rod are made of a flexible material, and the flexible material comprises phantom, rubber, silicone, plastic, nylon and resin.

6. The magnetism characteristic detection apparatus as claimed in claim 5, further comprising:
   an object temperature control device, coupled to the conduction device, and taking the conduction device as a control medium to control temperature of the object.

7. An imaging method, adapted to image at least one object, the imaging method comprises:
   applying a direct current magnetic field to the object to magnetize the object;
   providing an oscillation wave to the object to generate an oscillation on the object, wherein the oscillation wave is a sound wave or an ultrasound wave;
   scanning a magnetic flux of the object directly using an induction coil surrounding the object in order to obtain a variation of a magnetism characteristic of the object caused by the oscillation; and
   generating a magnetic imaging image related to the object according to the variation of the magnetism characteristic of the object.

8. The imaging method as claimed in claim 7, wherein the object is a biological organism or a targeted component in the biological organism.

9. The imaging method as claimed in claim 7, further comprising:
   detecting along a surface of the object to obtain a reflected oscillation wave generated by the object by reflecting the oscillation wave; and
   generating an oscillation wave imaging image related to the object according to the received reflected oscillation wave.

10. The imaging method as claimed in claim 9, wherein the oscillation wave is an ultrasound wave, and a frequency of the oscillation wave is not lower than 1000000 Hz.

11. An imaging apparatus, adapted to image at least one object, the imaging apparatus comprising:
    a direct current magnetic field generating device, applying a direct current magnetic field to the object to magnetize the object;
    an oscillation wave source, providing an oscillation wave to the object to generate an oscillation on the object, wherein the oscillation wave is a sound wave or an ultrasound wave;

an induction coil, scanning a variation of a magnetism characteristic of the object caused by the oscillation in a stationary or moving manner; and an image processing device, coupled to the induction coil, and generating a magnetic imaging image related to the object according to the variation of the magnetism characteristic of the object.

12. The imaging apparatus as claimed in claim 11, wherein the object is a biological organism or a targeted component in the biological organism.

13. The imaging apparatus as claimed in claim 11, further comprising:

an oscillation wave detection unit, coupled to the image processing device, and movably contacts with a surface of the object for detecting a reflected oscillation wave generated by the object by reflecting the oscillation wave, wherein the image processing device generates an oscillation wave imaging image related to the object according to the received reflected oscillation wave.

14. The imaging apparatus as claimed in claim 13, wherein the oscillation wave is an ultrasound wave, and a frequency of the oscillation wave is not lower than 1000000 Hz.

\* \* \* \* \*